United States Patent [19]

Farng et al.

[11] Patent Number: 5,643,584
[45] Date of Patent: Jul. 1, 1997

[54] AQUEOUS GEL RETINOID DOSAGE FORM

[75] Inventors: Richard K. Farng, East Brunswick; Gerard J. Gendimenico, Neshanic Station; James A. Mezick, East Brunswick; Shirley M. Ng, Bridgewater; Stanley B. Wrobel, Jr., Middlesex, all of N.J.

[73] Assignee: Ortho Pharmaceutical Corporation, Raritan, N.J.

[21] Appl. No.: 444,145

[22] Filed: May 18, 1995

Related U.S. Application Data

[63] Continuation of Ser. No. 132,014, Oct. 5, 1993, abandoned, which is a continuation of Ser. No. 869,684, Apr. 16, 1992, abandoned.

[51] Int. Cl.$^6$ .................................. A61K 7/00; A61K 7/48
[52] U.S. Cl. .......................... 424/401; 514/994; 514/947; 514/975; 514/859
[58] Field of Search .............................. 424/401; 514/844, 514/947, 847, 944, 975, 859; 568/824

[56] References Cited

U.S. PATENT DOCUMENTS

| | | | |
|---|---|---|---|
| 3,729,568 | 4/1973 | Kligman | 424/318 |
| 4,826,871 | 5/1989 | Gressel | 514/438 |
| 4,966,773 | 10/1990 | Gressel | 424/489 |
| 5,476,852 | 12/1995 | Cauwenbergh | 514/252 |

FOREIGN PATENT DOCUMENTS

| | | |
|---|---|---|
| 90/14082 | 11/1990 | WIPO . |
| 90/14833 | 12/1990 | WIPO . |

*Primary Examiner*—Sallie M. Gardner

[57] ABSTRACT

This invention relates to aqueous gel retinoid compositions and their methods of use. More specifically, the aqueous gel retinoid compositions of the invention utilize micronized particles of retinoids, particularly tretinoin, to provide an aqueous gel for topical application of such retinoids to the skin which minimizes skin irritation while retaining drug efficacy.

33 Claims, No Drawings

AQUEOUS GEL RETINOID DOSAGE FORM

This is a continuation, of application Ser. No. 08/132,014, filed Oct. 5, 1993, now abandoned, which is a 1.60 continuation of Ser. No. 07/869,684, now abandoned, filed Apr. 16, 1992, which are hereby incorporated by reference.

FIELD OF THE INVENTION

This invention relates to aqueous gel vehicles for retinoids. More specifically, micronized particles of retinoids, particularly tretinoin, are incorporated into aqueous gel vehicles to provide a gel composition for topical application of such retinoids to the skin.

BACKGROUND OF THE INVENTION

Retinoids (e.g. Vitamin A and its derivatives) are substances which are known to have a broad spectrum of biological activity. More specifically, these substances affect cell growth, differentiation and proliferation. Retinoids affect the differentiation, maintenance, and proliferation of many types of cells, whether they are of ectodermal, endodermal or mesodermal origin. Retinoids have found clinical utility in the treatment of acne vulgaris, severe cystic acne, psoriasis, and other disorders of keratinization. Possible uses of retinoids are being explored in the prophylaxis and treatment of cancer. See generally, Pawson, B. A. et al., "Retinoids at the Threshold: Their Biological Significance and Therapeutic Potential", *Journal of Medicinal Chemistry* 25:1269–1277 (1982).

It is known to use certain retinoids, particularly tretinoin, topically for treatment of acne as set forth in U.S. Pat. No. 3,729,568. Other known topical uses of tretinoin include, in addition to ache treatment, treatment of senile comedones, nevus comedonicus, linear verrucous nevus, plantar warts, pseudofolliculitis, keratoacanthoma, solar keratosis of extremities, callosities, keratosis palmaris et plantaris, Darier's disease, ichthyosis, psoriasis, acanthosis nigricans, lichen planus, molluscum contagiosum, reactive perforating collagenosis, melasma, corneal epithelial abrasion, geographic tongue, Fox-Fordyce disease, cutaneous metastatic melanoma and keloids or hypertrophic scars see, e.g., Thomas, J. R., et al., "The Therapeutic uses of Topical Vitamin A Acid", *Journal of American Academy of Dermatology* 4:505–516 (1981).

U.S. Pat. No. 4,603,146 discloses methods for treating sundamaged human skin topically with tretinoin in an emollient vehicle. U.S. Pat. Nos. 4,877,805 and 4,883,342 disclose methods for the treatment of sundamaged human skin using retinoids. U.S. Pat. No. 5,051,449 discloses treatment of cellulite with retinoids.

The above-noted patents disclose formulations of retinoids in various moisturizing bases such as creams or ointments. Retinoids, such as tretinoin, in cream formulations, may meet the needs of certain individuals but may be found undesirable by other individuals. It is also suggested in European Patent Application No. 90303826.3 to Maxam, Inc. that volatile vehicles, such as alcohols, which may dry or otherwise harm the skin should be avoided. Maxam's patent application discloses an aqueous gel formulation of tretinoin which utilizes a glycerin and a proteinaceous material, e.g. soluble animal collagen, to stabilize its gelling agent. The present invention does not require the use of glycerin nor a proteinaceous material to stabilize its gel formulation.

SUMMARY OF THE INVENTION

It is therefore an object of the present invention to provide a retinoid aqueous gel composition for topical administration of retinoid to the skin which minimizes skin irritation but maintains a high degree of therapeutic effectiveness.

As embodied and fully described herein, the present invention provides a retinoid aqueous gel composition for therapeutic topical administration of retinoid to the skin comprising a therapeutically effective amount of micronized retinoid particles; a surfactant in an amount effective to enhance penetration of retinoid into the skin; a preservative; a gelling agent composition in an amount sufficient to provide body to the aqueous gel; and water qs to 100%. In preferred embodiments the composition comprises in weight by total weight of the composition: 0.0001 to 0.5% micronized retinoid particles; 0.001 to 1.0% surfactant; 0.005 to 2.0% preservative; 0.01% to 0.3%. antioxidant; 1.0% to 2.0% gelling agent; sufficient base to attain a pH in the range of 4.0 to 7.0; and water qs to 100%.

In preferred embodiments of the invention, the retinoid is tretinoin. In other preferred embodiments, the micronized particles comprise at least 90% of the particles in a size range of from 1 to 40 microns, more preferably from 1 to 30 microns, and most preferably with a mean size in the range of 1 to 10 microns. In preferred embodiments the surfactant of the aqueous gel composition is selected from the group consisting of: octoxynol, polyethylene glycol glyceryl stearate and nonoxynol. In preferred embodiments the preservative is selected from the group consisting of benzyl alcohol, sorbic acid, pardbens, imidazolidinyl urea (imidurea) and combinations thereof, more preferably, a combination of benzyl alcohol and sorbic acid. In preferred embodiments of the composition, the gelling agent is selected from the group consisting of acrylic acid crosslinked with the allyl ether of sucrose or pentaerythritol; and poloxamer. Preferably, the gelling agent is an acrylic acid polymer known to the art as carbomer. In preferred embodiments of the invention, the base used to raise the pH of the composition to a pH of between 4.0 to 7.0 is sodium hydroxide or triethanolamine, preferably, sodium hydroxide which is added in an amount of about 0.1% to 0.6% to provide a pH to the composition of between 4.5 to 5.5. In preferred embodiments of the invention the antioxidant is butylated hydroxytoluene (BHT), butylated hydroxyanisole (BHA), alpha-tocopherol, or ascorbic acid. In preferred embodiments of the invention the aqueous gel composition comprises from about 0.0001% to 0.5% retinoid, preferably, 0.01% to 0.2% retinoid.

In a preferred embodiment of the invention the aqueous gel composition does not contain any water soluble lower alkyl alcohol.

In other embodiments of the aqueous gel of the invention polyvinylpyrrolidone is added thereto to inhibit crystal growth of the micronized retinoids. In further preferred embodiments a chelating agent is added thereto.

Methods of using the aqueous gel composition of the invention are provided to increase the therapeutic effectiveness of retinoids for topical application to the skin comprising the step of delivering a dispersion of micronized retinoid particles in an aqueous gel vehicle to the intended site of skin application. In preferred embodiments of the invention the method provides for delivering micronized retinoid to an intended site of application using an aqueous gel vehicle which has an alcohol content of less than 2% by weight of the total weight of the composition, more preferably the aqueous gel vehicle contains no water soluble lower alkyl alcohol.

In other embodiments of the invention a method is provided for reducing the irritation associated with retinoid therapy which comprises the steps of incorporating micronized retinoid in an aqueous gel vehicle and applying the micronized retinoid aqueous gel composition to the skin of a patient. In preferred embodiments the aqueous gel composition used in this method comprises any of the preferred embodiments of the formulation described above.

DETAILED DESCRIPTION OF PREFERRED EMBODIMENTS OF THE INVENTION

Reference will now be made in detail to preferred embodiments of the invention. Examples of the preferred embodiments are illustrated in the following Examples section.

Retinoids have been defined narrowly as comprising vitamin A (retinol) and its derivatives, such as vitamin A aldehyde (retinal) and vitamin A acid (tretinoin), which are metabolites of vitamin A. Subsequent research has, however, resulted in a larger class of chemical compounds that are termed retinoids because they have biological actions similar to vitamin A, even though there may be structural dissimilarities. Compounds useful in the present invention include all natural and/or synthetic analogs of vitamin A or retinol-like compounds which have similar therapeutic activities as demonstrated for example, by tretinoin. Accordingly, as used herein for purposes of the present invention, the term "retinoid" will be understood to mean a natural or synthetic substance that elicits all or some of the biologic responses of retinoic acid or retinol by binding to and subsequently activating known and unknown cutaneous retinoic acid receptors. Also encompassed within the term "retinoid" for the purposes of the present invention, are stereoisomers of the retinoids, as well as pro-drugs thereof. Examples of retinoids include those disclosed in U.S. Pat. No. 4,877,805, the entire disclosure of this patent is hereby incorporated herein by reference.

The present invention provides an aqueous gel composition for topical administration of retinoids to the skin which increases the therapeutic effectiveness of such an application over alcoholic gel vehicles or oil-based vehicles while reducing the irritation that is associated with the applications of retinoids to the skin of certain sensitive patients.

The aqueous gel composition of the invention also provides for increasing the safety of topically applied retinoid to the skin whereby micronized retinoids are provided to an intended site of application using an aqueous gel vehicle which preferably contains no lower alkyl alcohols. This elimination of lower alkyl alcohol reduces potential problems of drying the skin as well as reducing volatile fumes which may be undesirably inhaled or be flammable during production of alcohol gel products.

The aqueous gel composition of the invention comprises at least one retinoid in accordance with the definition described above. In preferred embodiments of the invention the retinoid is tretinoin. The retinoid, preferably tretinoin, is provided in a micronized form whereby at least 90% of the retinoid particles are provided in the size range of 1 to 40 microns, more preferably 1 to 30 microns. Most preferably, the micronized retinoid particles have a mean size in the range of 1 to 10 microns. The retinoid particles which normally average above 40 microns to about 100 microns in size are reduced in particle size, i.e. micronized in accordance with procedures known to the art such as using fluid-energy mills.

The aqueous gel composition of the invention comprise in weight by total weight of the composition of from about 0.0001 to 0.5% micronized retinoid, preferably tretinoin, particles. In more preferred embodiments micronized tretinoin is present in the range of 0.005 to 0.2%. This concentration range is particularly advantageous for topical application of retinoid and particularly tretinoin particles to the skin of a patient because it provides optimal effective amounts of retinoid to the skin for treatment of acne and/or treatment of sundamaged skin and other therapeutic applications. Using tretinoin as a standard for retinoids, tretinoin will typically be present in the composition of the invention in an amount of about 0.001 to 0.5, preferably 0.005 to 0.2% weight by total weight, and other more or less potent retinoids will be used in corresponding amounts equivalent thereto.

Larger amounts of retinoid, e.g. tretinoin, present in the formulations may increase the chance for skin irritation. Amounts which are less than those provided in this range may not provide enough retinoid or tretinoin to provide effective treatment to the skin of a patient.

The retinoid aqueous gel composition of the invention comprises from about 0.001% to 1.0% surfactant, weight by total weight of the composition. The surfactant is useful to enhance the penetration of the retinoid into the epidermis layer of the skin and also to disperse the retinoid particles throughout the aqueous media. This dispersion is important to provide consistent dosage forms and applications of the drugs for application of optimal treatments to the skin of patients. Surfactants which are useful in accordance with the invention include but are not limited to those selected from the group consisting of octoxynol (an anhydrous mixture of mono [p-(1,1,3,3,-tetra-methylbutyl)phenyl]ethers of polyethylene glycols containing 5 to 15 oxyethylene groups in the polyoxyethylene chain), polyethylene glycol glyceryl stearate and nonoxynol. Particularly preferred as a surfactant is octoxynol-13 (whereby an average of 13 oxyethylene groups are in the polyoxyethylene chain).

The aqueous gel composition of the invention preferably comprises from about 0.005% to 2.0% preservative weight by total weight of the composition. The preservative is used to prevent spoilage of the aqueous gel during repeated patient use when it is exposed to contaminants in the environment from, for example, exposure to air or the patient's skin including contact with the fingers used for applying the therapeutic gel. Examples of preservatives useful in accordance with the invention include but are not limited to those selected from the group consisting of benzyl alcohol, sorbic acid, parabens, imidurea and combinations thereof. A particularly preferred preservative is a combination of about 0.5%-2.0% benzyl alcohol and 0.05% to 0.5% sorbic acid.

The aqueous gel composition preferably includes an antioxidant and a chelating agent which inhibit the degradation of the retinoid in the aqueous gel formulation. Preferred antioxidants are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively, other suitable and equivalent antioxidants and chelating agents may be substituted therefor as would be known to those skilled in the art.

The aqueous gel composition of the invention comprises a gelling agent which provides body to the aqueous gel vehicle and maintains the dispersion of retinoids in the vehicle by maintenance of the semisolid dosage form. Particularly preferred gelling agents are selected from the group consisting of acrylic acid polymers cross-linked with polyalkylsucrose; and poloxamer. More particularly, the gelling agent is an acrylic acid polymer crosslinked with the allyl ether of sucrose or pentaerythritol which are generally known as carbomers. Carbomers are sold under the trademark CARBOPOL, in various grades. The more useful grades for the purposes of the present invention are 934, 934P, 940, 941, 980 and 981 with 940 being the most preferred. These numbers designate the molecular weight and the crosslinking of the carboxypolymethylene molecules. Carbomers are referenced and listed in USP XXII, 1910–1912 (1990). While the gelling agents specifically identified above are presently preferred, other suitable and equivalent gelling agents may be substituted therefor as would be known to those skilled in the art.

In other optional embodiments of the invention polyvinylpyrrolidone is added to the aqueous gel composition of the invention to inhibit crystal growth of the micronized retinoid and particularly, tretinoin. Optionally, about 0.1% to 1.0%, and more preferably, 0.3% of polyvinylpyrrolidone by weight by total weight of the composition is added to the aqueous gel. Further, other additives such as about 5% to 20% hydroxypropyl-beta-cyclodextrin (HPBCD) may be added to the formulation to enhance the availability of retinoid to the skin with reduced irritation.

To achieve proper gelling of the formulation, the acidic carbomer gelling agent component is neutralized by the addition of a base thereto to form a gelling composition which provides body to the gel dosage form. In preferred embodiments enough base is added to the carbomer containing aqueous gel compositions of the invention to provide a pH of between 4.0 and 7.0, more preferably 4.5 to 5.5. While any suitable base may be used the preferred bases used to raise the pH of the aqueous gels of the invention are sodium hydroxide and triethanolamine. The exact amount of sodium hydroxide or triethanolamine that is added to an aqueous gel to achieve the desired pH range depends upon the amount of carbomer that is present in the aqueous gel composition. Generally, about 0.1% to 0.6% of pure sodium hydroxide by weight by total weight of the composition is added to provide a pH of the aqueous gel composition of the invention of between 4.0 and 7.0, more preferably 4.5 to 5.5. Sodium hydroxide may be added to the aqueous gel compositions by means of a 10% aqueous solution for ease of handling and mixing.

It is preferable in the aqueous gel composition of the invention to eliminate the presence of any water soluble alcohol such as isopropyl alcohol or ethanol from the formulation to prevent the potential deleterious affects of such alcohols, e.g. undesirable drying of the skin. While benzyl alcohol is a preferred antimicrobial preservative which is provided in amounts of about 0.5% to 2.0% by weight by total weight of the invention, it is not intended as a solubilizing alcohol as distinguished from water soluble alkyl alcohols which are intended as solubilizers for retinoids e.g. isopropanol or ethanol. The aqueous gel vehicle of the invention advantageously provides micronized retinoid as a dispersion and not a solution for topical application.

The use of micronized retinoids and/or tretinoin particles represent a significant aspect of the present invention. The use of micronized particles of a water insoluble retinoid permits the use of an aqueous gel vehicle containing no solubilizing alcohol (e.g. no water soluble lower alkyl alcohol), to provide otherwise unattainable amounts of topical availability and penetration of retinoid into the skin. The dispersion of the "extremely fine" micronized particles achieve good penetration of the retinoid into the skin without significant passing of retinoid through the skin.

Additional medicaments or active components may be used in combination with the retinoid dosage form composition of the invention. For example, antibiotics used in acne preparations such as: the antibacterials erythromycin, clindamycin, tetracycline, minocycline, of loxacin and sodium sulfacetamide; antifungals such as miconazole, terconazole, ketoconazole, econazole, fluconazole and clotrimazole; corticosteriods such as triamcinolone, betamethasone and clobetasol; as well as other actives such as sulfur, anthralin, azelaic acid, alpha-hydroxy acids, benzoyl peroxide and skin growth factors; salts and derivatives of all of the above; and mixtures of any of the above may be added to the retinoid dosage form of the invention.

As will be discussed below in the Examples section and the evaluation thereof, the aqueous gel formulations of the invention utilizing micronized tretinoin particles dispersed in formulation components provide for increased therapeutic effectiveness of tretinoin for topical application to human skin. This result is unexpected and surprising in view of the state of the prior art which is focused on solubilizing retinoids in topical formulations. The present invention surprisingly achieves excellent topical skin penetration of retinoids in an aqueous dispersion while reducing deleterious side effects, e.g. irritation, thus improving the therapeutic index of the composition of the invention over those retinoid preparations of the prior art.

The invention will now be illustrated by examples. The examples are not intended to be limiting of the scope of the present invention but read in conjunction with the detailed and general description above, provide further understanding of the invention and outline a process for preparing the compositions of the inventions and methods of practicing the invention.

EXAMPLES

The following ingredients, processes and procedures for preparing the compositions of the present invention correspond to that described above. The procedures below describe with particularity the various formulation ingredients and procedures utilized. Any methods, starting materials, reagents or excipients which are not particularly described will be generally known and available to those skilled in the pharmaceutical formulation arts. All formulation percentages are provided in percentage by weight by total weight of the composition.

Example 1

Micronized tretinoin (0.0001–0.1%)aqueous gels with a preferred preservative system:

| | |
|---|---|
| micronized tretinoin | 0.0001–0.1% |
| octoxynol-13 (IGEPAL*CA-720) | 0.2% |
| sorbic acid | 0.1% |
| benzyl alcohol | 1.0% |
| disodium edetate | 0.05% |
| ascorbic acid | 0.1% |
| sodium metabisulfite | 0.2% |
| carbomer (CARBOPOL 940) | 1.5% |
| sodium hydroxide | 0.2% |
| purified water qs | 100% |

The aqueous gel of Example 1 was evaluated in an in vivo comparative study against a conventional alcohol gel. A formulation of a commercially available alcoholic gel in either of two strengths, 0.025% or 0.01% tretinoin, (vitamin A acid) by weight, comprises butylated hydroxytoluene, hydroxypropyl cellulose and alcohol in a gel vehicle. This formulation is utilized throughout the Examples section and designated as "Alcohol Gel (Comparative)". An evaluation and comparative of the aqueous gel of the invention and this conventional alcohol gel is provided below. The tests were carried out in accordance with the protocol and systems provided and explained in U.S. Pat. No. 4,487,782 and Mezick et al., "Topical and Systemic Effects of Retinoids on Horn-Filled Utriculus Size in the Rhino Mouse. A Model to Quantify 'Antikeratinizing' Effects of Retinoids", Journal of Investigative Dermatology, 83:110–113(1984), the entire disclosure of which is hereby incorporated herein by reference.

In the following formulation evaluation $ED_{50}$ refers to measurements of efficacy (50% utriculus reduction); $ID_{50}$ refers to irritation (50% of maximum erythema grade of 3.0); Rel. Potency is relative potency and F.L. is the fiducial limit.

| Rhino Mouse Utriculus Reduction Alcohol Gel (Comparative) | | | |
|---|---|---|---|
| Dose % | % Utriculus Reduction | $ED_{50}$ | Rel. Potency (95% F.L.) |
| 0.0001 | 6.5 | | |
| 0.001 | 21.1 | 0.008 | 1 |
| 0.01 | 55.2 | | |
| 0.05 | 69.5 | | |
| Aqueous Gel (Example 1) | | | |
| 0.0001 | 18.1 | | |
| 0.001 | 31.6 | 0.006 | 1.7 (1.2, 2.6) |
| 0.01 | 53.9 | | |
| 0.05 | 69.1 | | |

| Rabbit Dermal Irritation Alcohol Gel (Comparative) | | | |
|---|---|---|---|
| Dose % | Erythema Grade | $ID_{50}$ | Rel. Potency (95% F.L.) |
| 0.001 | 0.5 | | |
| 0.01 | 1.3 | 0.007 | 1 |
| 0.05 | 2.8 | | |
| Aqueous Gel (Example 1) | | | |
| 0.01 | 0.6 | | |
| 0.05 | 1.1 | 0.1 | 0.09 (0.05, 0.16) |
| 0.1 | 1.6 | | |

The aqueous gel of Example 1 is found to be more potent than the comparative alcohol gel on utriculus reduction, as demonstrated by the lower $ED_{50}$ for the aqueous gel and much less irritating to rabbit skin as indicated by the higher tolerated dose at $ID_{50}$ for the aqueous gel. The therapeutic index comprising the ratio of $ID_{50}/ED_{50}$ (T.I.) for the aqueous gel of the invention is 0.1/0.006 (T.I.=17) vs. the comparative alcohol gel which is 0.007/0.008 (T.I.=1).

Example 2

| | |
|---|---|
| tretinoin | 0.025% |
| octoxynol-13 (IGEPAL*CA-720) | 0.2% |
| sorbic acid | 0.1% |
| benzyl alcohol | 1.0% |
| disodium edetate | 0.05% |
| alpha-tocopherol | 0.04% |
| carbomer (CARBOPOL 940) | 1.5% |
| sodium hydroxide | 0.2% |
| purified water qs | 100% |

This formulation was tested for the extent of tretinoin penetration into human skin in vitro. The following procedure is used for investigating the in vitro skin permeation of tretinoin from the aqueous and alcoholic gel formulations:

Human skin samples were kept frozen at −70° C. until use. Samples were thawed at room temperature for 30 minutes, and then rinsed with normal saline. Skin samples were cut into appropriate sized pieces, tared, a 1 mm thick film of formulation was applied, and the samples were weighed. The skin was then mounted on a diffusion cell (modified Franz diffusion cells, 9 mm opening, 10 ml volume), which had previously been filled with receptor medium (10% HPBCD in water). Upon completion of the study (24 hours), the receptor medium was sampled. The excess formulation was wiped from the skin surface using a Kim-Wipe soaked in acetone, the skin surface was washed twice with water and once with acetone, wiping the skin surface with a Kim-Wipe after each wash. Each skin sample was placed into a volumetric flask and tretinoin was extracted.

The skin samples were extracted with methanol:ethyl acetate (1:1) with 0.5% BHT. Samples were sonicated 45 minutes and a portion of the extracts were then assayed by HPLC.

The results of the in vitro skin permeation of tretinoin from the formulation of Example 2 as compared to alcoholic gel (comparative) and two other comparative formulations whereby the formulation of Example 2 was altered to exclude the surfactant and to substitute unmicronized particles of tretinoin for micronized particles are all summarized below:

| Formulation | Amount in Skin | Amount Passing Through Skin |
|---|---|---|
| Alcoholic Gel (comparative) | 18 +/− 2 mcg | 0.4 mcg |
| Aqueous Gel (Ex. 2) | 30 +/− 1 mcg | 0.0 mcg (below detection limit) |
| Aqueous Gel (Ex. 2) without surfactant | 9.3 +/− 2 mcg | 0.0 mcg |
| Aqueous Gel (Ex. 2) with large (unmicronized) tretinoin particles | 18 +/− 2 mcg | 0.0 mcg |

The tretinoin aqueous gel of the present invention releases tretinoin into the upper layer of human skin but not any detectable amount passes through the skin. This example of an aqueous gel of the invention thus releases tretinoin into the skin as well as or better than the commercially available alcoholic gels without excess drug passing through the skin and without excess irritation.

Further investigation of the aqueous gels of the invention versus comparison gels not containing a surfactant or containing larger (unmicronized) particles of tretinoin indicates a drop in skin permeation of tretinoin of approximately 3-fold and 2-fold respectively. Such results indicate that the use of a surfactant and micronized particles of tretinoin contribute to a surprising enhancement of tretinoin skin permeation from the aqueous gel formulations of the invention.

Example 3

Micronized tretinoin (0.0001–0.1%) aqueous gels with polyvinylpyrrolidone:

| | |
|---|---|
| micronized tretinoin | 0.0001–0.1% |
| octoxynol-13 (IGEPAL*CA-720) | 0.2% |
| methyl paraben | 0.18% |
| propyl paraben | 0.02% |
| benzyl alcohol | 1.0% |
| disodium edetate | 0.05% |
| ascorbic acid | 0.1% |
| polyvinylpyrrolidone | 0.3% |
| carbomer (CARBOPOL*934) | 1.5% |
| sodium hydroxide | 0.16% |
| purified water qs | 100% |

Formulation Evaluation

| Rhino Mouse Utriculus Reduction Alcohol Gel (Comparative) | | | |
|---|---|---|---|
| Dose % | % Utriculus Reduction | $ED_{50}$ | Rel. Potency (95% F.L.) |
| 0.0001 | 12.0 | | |
| 0.001 | 28.5 | 0.004 | 1 |
| 0.01 | 64.4 | | |
| 0.05 | 77.1 | | |
| Aqueous Gel (Example 3) | | | |
| 0.0001 | 7.9 | | |
| 0.001 | 31.6 | 0.004 | 0.9 (0.7, 1.1) |
| 0.01 | 59.6 | | |
| 0.05 | 76.5 | | |

| Rabbit Dermal Irritation Alcohol Gel (Comparative) | | | |
|---|---|---|---|
| Dose % | Erythema Grade | $ID_{50}$ | Rel. Potency (95% F.L.) |
| 0.001 | 0.1 | | |
| 0.01 | 0.9 | 0.01 | 1 |
| 0.05 | 2.6 | | |
| Aqueous Gel (Example 3) | | | |
| 0.001 | 0 | | |
| 0.01 | 0.3 | 0.06 | 0.3 (0.1, 0.7) |
| 0.05 | 1.9 | | |

This aqueous gel is found to be as potent as the alcohol gel on utriculus reduction, but was much less irritating to rabbit skin (aqueous gel T.I.=15 vs. alcohol gel T.I.=2.5).

Example 4

| | |
|---|---|
| micronized tretinoin | 0.0001–0.1% |
| octoxynol-13 (IGEPAL* CA-720) | 0.2% |
| disodium edetate | 0.02% |
| ascorbic acid | 0.1% |
| imidurea (GERMALL* 115) | 0.4% |
| polyvinylpyrrolidone | 0.3% |
| hydroxypropyl-beta-cyclodextrin | 10.0% |
| carbomer (CARBOPOL* 940) | 1.5% |
| sodium hydroxide | 0.18% |
| purified water qs | 100% |

Formulation Evaluation

| Rhino Mouse Utriculus Reduction Alcohol Gel (Comparative) | | | |
|---|---|---|---|
| Dose % | % Utriculus Reduction | $ED_{50}$ | Rel. Potency (95% F.L.) |
| 0.0001 | 12.7 | | |
| 0.001 | 26.6 | 0.004 | 1 |
| 0.01 | 63.9 | | |
| 0.05 | 76.2 | | |
| Aqueous Gel (Example 4) | | | |
| 0.0001 | 12.5 | | |
| 0.001 | 23.2 | 0.005 | 0.9 (0.6, 1.4) |
| 0.01 | 64.8 | | |
| 0.05 | 75.0 | | |

| Rabbit Dermal Irritation Alcohol Gel (Comparative) | | | |
|---|---|---|---|
| Dose % | Erythema Grade | $ID_{50}$ | Rel. Potency (95% F.L.) |
| 0.001 | 0.1 | | |
| 0.01 | 0.9 | 0.01 | 1 |
| 0.05 | 2.6 | | |
| Aqueous Gel (Example 4) | | | |
| 0.001 | 0 | | |
| 0.01 | 0.3 | 0.12 | 0.2 (0.08, 0.5) |
| 0.1 | 1.6 | | |

The above aqueous gel is found to be as potent as the alcohol gel on utriculus reduction, but was much less irritating to rabbit skin (aqueous gel T.I.=24 vs. alcohol gel T.I.=2.5).

Example 5

| | |
|---|---|
| micronized tretinoin | 0.0001–0.5% |
| octoxynol-13 (IGEPAL* CA720) | 0.2% |
| sorbic acid, NF | 0.1% |
| benzyl alcohol, NF | 1.0% |
| disodium edetate, NF | 0.05% |
| citric acid, USP | 0.1% |
| butylated hydroxytoluene, NF | 0.05% |
| carbomer (CARBOPOL* 940), NF | 1.5% |
| sodium hydroxide, USP | 0.2% |
| purified water, USP qs | 100% |

The above tretinoin aqueous gel composition is expected to provide similar advantageous results analogous to those formulations of the invention evaluated above.

The above evaluations and test results demonstrate the utility of the formulations of the invention for increasing the effective therapeutic index, i.e. $ID_{50}/ED_{50}$ for topical administration of retinoids, particularly, tretinoin on the skin of a patient. The increased therapeutic index is achieved by requiring higher amounts of active (retinoid) to produce a specific threshold of irritation ($ID_{50}$) and lower amounts to produce a specific threshold of efficacy ($ED_{50}$) in the aqueous gel formulations of the invention.

The scope of the present invention is not limited by the description, examples and suggested uses herein and modifications can be made without departing from the spirit of the invention. The formulations of the invention may, for example, have other applications and uses in addition to those described herein.

Applications of the compositions and methods of the present invention for medical or pharmaceutical uses can be accomplished by any clinical, medical, and pharmaceutical methods and techniques as are presently or prospectively known to those skilled in the art. Thus it is intended that the invention cover any modifications and variations of this invention provided that they come within the scope of the appended claims and their equivalents.

What is claimed is:

1. A tretinoin aqueous gel dispersion composition for therapeutic topical administration of tretinoin to the skin comprising: a therapeutically effective amount of unsolubilized micronized tretinoin particles; a surfactant selected from the group consisting of octoxynol and nonoxynol in an amount effective to enhance penetration of tretinoin into the skin; a preservative; a gelling agent in an amount sufficient to provide body to the aqueous gel dosage form skin and which maintains the dispersion of tretinoin in the composition by maintenance of a semisolid dosage form; and water qs to 100%.

2. A tretinoin aqueous gel dispersion composition for topical administration of tretinoin to the skin comprising in weight by total weight of the composition: 0.001 to 0.5% micronized tretinoin particles; 0.001 to 1.0% surfactant selected from the group consisting of octoxynol and nonoxynol; 0.005 to 2.0% preservative; 0.01% to 0.3% antioxidant; 1.0% to 2.0% of a gelling agent; sufficient base to attain a pH in the range of from 4.0 to 7.0; and water qs to 100%.

3. An aqueous gel composition according to claim 1 wherein the preservative is selected from the group consisting of: benzyl alcohol, sorbic acid, parabens, imidurea and combinations thereof.

4. An aqueous gel composition according to claim 1 wherein the gelling agent is selected from the group consisting of: acrylic acid polymer crosslinked with allyl ether of sucrose or pentaerythritol; and poloxamer.

5. An aqueous gel composition according to claim 1 wherein the micronized tretinoin comprises at least 90% of the particles in the size range of 1 to 30 microns.

6. An aqueous gel composition according to claim 1 wherein the micronized tretinoin particles have a mean size in the range of 1 to 10 microns.

7. An aqueous gel composition according to claim 1 wherein polyvinylpyrrolidone is added in an amount effective to inhibit crystal growth of the micronized tretinoin.

8. An aqueous gel composition according to claim 2 wherein the micronized tretinoin is present in the range of 0.005 to 0.2%.

9. An aqueous gel composition according to claim 2 wherein the surfactant is present in the range of 0.01 to 0.5%.

10. An aqueous gel composition according to claim 1 additionally comprising a chelating agent.

11. An aqueous gel composition according to claim 1 additionally comprising hydroxypropyl-beta-cyclodextrin.

12. An aqueous gel composition according to claim 2 wherein the base used to lower the pH of the composition to a pH between 4.0 to 7.0 is sodium hydroxide or triethanolamine.

13. An aqueous gel composition according to claim 1 wherein about 0.1 to 0.6% sodium hydroxide is added to provide a pH to the composition of between 4.5 to 5.5.

14. An aqueous gel composition according to claim 2 wherein the antioxidant is selected from the group consisting of: alpha-tocopherol, butylated hydroxytoluene, butylated hydroxyanisole and ascorbic acid.

15. An aqueous gel composition according to claim 1 which does not contain any water soluble lower alkyl alcohol.

16. A method of increasing the therapeutic effectiveness of tretinoin for topical application to the skin comprising the step of delivering micronized tretinoin dispersed in an aqueous gel vehicle containing a surfactant selected from the group consisting of octoxynol and nonoxynol to the intended site of skin application.

17. A method of increasing the therapeutic effectiveness of tretinoin for topical skin application comprising the step of delivering micronized tretinoin to the intended site of application using an aqueous gel dispersion composition in accordance with claim 1.

18. The method of claim 17 wherein the aqueous gel composition contains no water soluble lower alkyl alcohol.

19. A method of improving the skin penetration of a topically administered tretinoin to the skin of a patient comprising the steps of:

dispersing micronized tretinoin in an aqueous gel composition in accordance with claim 1; and applying the tretinoin aqueous gel to the skin of a patient.

20. A method of reducing irritation associated with the topical administration of tretinoin to a patient comprising the steps of:

dispersing micronized tretinoin in an aqueous gel composition in accordance with claim 1; and applying the micronized tretinoin aqueous gel to the skin of a patient.

21. A retinoid aqueous gel composition for therapeutic topical administration of retinoid to the skin comprising: a therapeutically effective amount of unsolubilized micronized retinoid particles; a surfactant selected from the group consisting of octoxynol and nonoxynol in an amount effective to enhance penetration of retinoid into the skin; a preservative; a gelling agent composition in an amount sufficient to provide body to the aqueous gel dosage form and which maintains the dispersion of retinoids in the composition by maintenance of a semisolid dosage form; and water qs to 100%.

22. A retinoid aqueous gel dispersion composition for topical administration of retinoid to the skin comprising in weight by total weight of the composition: 0.001 to 0.5% micronized unsolubilized retinoid particles; 0.001 to 1.0% surfactant selected from the group consisting of octoxynol and nonoxynol; 0.005 to 2.0% preservative; 0.01% to 0.3% antioxidant; 1.0% to 2.0% of a gelling agent; sufficient base to attain a pH in the range of from 4.0 to 7.0; and water qs to 100%.

23. An aqueous gel composition according to claim 21 wherein the micronized retinoid comprises at least 90% of particles in the range of from in 1 to 30 microns.

24. An aqueous gel composition according to claim 21 wherein the micronized retinoid particles have a mean size in the range of 1 to 10 microns.

25. An aqueous gel composition according to claim 21 additionally comprising a chelating agent.

26. An aqueous gel composition according to claim 22 wherein the chelating agent is selected from the group consisting of disodium edetate and citric acid.

27. A method of increasing the therapeutic effectiveness of retinoid for topical application to the skin comprising the step of delivering micronized retinoid dispersed in an aqueous gel vehicle containing a surfactant selected from the group consisting of octoxynol and nonoxynol to the intended site of skin application.

28. The method of claim 27 wherein the aqueous gel vehicle contains no water soluble lower alkyl alcohol.

29. A tretinoin aqueous gel dispersion composition for therapeutic topical administration of tretinoin to the skin consisting essentially of in weight by total weight of the composition: 0.001 to 0.5% micronized unsolubilized tretinoin particles; 0.001 to 1.0% surfactant selected from the group consisting of octoxynol and nonoxynol; 0.005 to 2.0% preservative; 0.01% to 0.3% antioxidant; 1.0% to 2.0% of a gelling agent; sufficient base to attain a pH in the range of from 4.0 to 7.0; and water.

30. A retinoid aqueous gel dispersion composition for therapeutic topical administration of retinoid to the skin consisting essentially of a therapeutically effective amount of unsolublized micronized retinoid particles; a surfactant selected From the group consisting of octoxynol and nonoxynol in an amount effective to enhance penetration of retinoid into the skin; a preservative; a gelling agent composition in an amount sufficient to provide body to the aqueous gel dosage form; and water.

31. A method for reducing irritation associated with the topical administration of tretinoin to the skin of a patient comprising:
    (a) dispersing in a composition for topical administration in weight by total weight of the composition: 0.001 to 0.5% micronized unsolubilized tretinoin particles; 0.001 to 1.0% surfactant selected from the group consisting of octoxynol and nonoxynol; 0.005 to 2.0% preservative; 0.01% to 0.3% antioxidant; 1.0% to 2.0% of a gelling agent; sufficient base to attain a pH in the range of from 4.0 to 7.0; and water; and
    (b) applying said composition to the skin of a patient.

32. A method for reducing irritation associated with the topical administration of a retinoid to the skin of a patient comprising:
    (a) dispersing in a composition for topical administration in weight by total weight of the composition: 0.001 to 0.5% micronized unsolubilized retinoid particles; 0.001 to 1.0% surfactant selected from the group consisting of octoxynol and nonoxynol; 0.005 to 2.0% preservative; 0.01% to 0.3% antioxidant; 1.0% to 2.0% of a gelling agent; sufficient base to attain a pH in the range of from 4.0 to 7.0; and water; and
    (b) applying said composition to the skin of a patient.

33. A method for reducing irritation associated with the topical administration of a retinoid to the skin of a patient while maintaining therapeutic effectiveness of said retinoid comprising:
    (a) dispersing in a composition for topical administration comprising: a therapeutically effective mount of micronized retinoid particles; a surfactant selected from the group consisting of octoxynol and nonoxynol in an amount effective to enhance penetration of retinoid into the skin; a preservative; a gelling agent composition in an amount sufficient to provide body to the aqueous gel dosage form; and water qs to 100%; and
    (b) applying said composition to the skin era patient.

* * * * *